United States Patent [19]

Schlecker et al.

[11] Patent Number: 5,151,437

[45] Date of Patent: Sep. 29, 1992

[54] BENZOFURANCARBOXAMIDES HAVING BASIC SUBSTITUENTS AND THERAPEUTIC AGENTS CONTAINING THE SAME

[75] Inventors: Rainer Schlecker, Bissersheim; Hans-Juergen Teschendorf, Dudenhofen; Liliane Unger, Ludwigshafen, all of Fed. Rep. of Germany

[73] Assignee: BASF Aktiengesellschaft, Ludwigshafen, Fed. Rep. of Germany

[21] Appl. No.: 598,785

[22] Filed: Oct. 15, 1990

Related U.S. Application Data

[63] Continuation of Ser. No. 221,653, Jul. 20, 1988, abandoned.

[30] Foreign Application Priority Data

Jul. 25, 1987 [DE] Fed. Rep. of Germany ....... 3724756

[51] Int. Cl.⁵ .................... C07D 207/09; A61K 31/40
[52] U.S. Cl. ...................................... 514/320; 546/196
[58] Field of Search .......................... 514/320; 546/196

[56] References Cited

U.S. PATENT DOCUMENTS 4,113,951  9/1978  Bourgery et al. .................. 546/196
4,617,314 10/1986  Tahara et al. ...................... 546/196

FOREIGN PATENT DOCUMENTS

A0147044 11/1984  European Pat. Off.
3724756  7/1987  Fed. Rep. of Germany
A2578369  3/1985  France

OTHER PUBLICATIONS

*Organic Chemistry*, Solomons, T.W.G., 1984 p. 800.
Arzneimittel Forschung, Band 21, Nr. 7, Jul. 1971, Seiten 1026-1028, Aulendorf, De: O. H. Hishmat et al.: "Synthesis of some benzofuran-carboxamide" ...

*Primary Examiner*—C. Warren Ivy
*Assistant Examiner*—Catherine Scalzo
*Attorney, Agent, or Firm*—Oblon, Spivak, McClelland, Maier & Neustadt

[57] ABSTRACT

A benzofurancarboxamide of the formula:

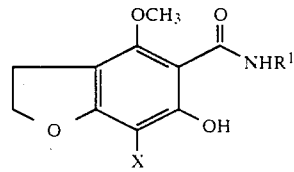

where:
X is hydrogen or methoxy,
$R^1$ is a radical of the formula:

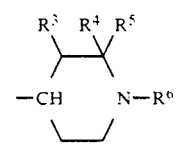

wherein $R^3$ to $R^5$ are each, independently of one another, hydrogen or $C_{1-6}$ alkyl, $R^6$ is a branched or unbranched $C_{1-6}$ alkyl, or benzyl which may be methyl- or halogen-substituted on the nucleus, and ∥ is a single or double bond.

13 Claims, No Drawings

BENZOFURANCARBOXAMIDES HAVING BASIC SUBSTITUENTS AND THERAPEUTIC AGENTS CONTAINING THE SAME

This application is a continuation of application Ser. No. 07/221,653, filed on Jul. 20, 1988, now abandoned.

FIELD OF THE INVENTION

The present invention relates to novel benzofurancarboxamides having basic substituents, to a process for the preparation thereof, and to therapeutic agents containing them, especially for the therapy of a number of disorders of the central nervous system, exogenous psychological disturbances and dyskinesias.

DISCUSSION OF THE BACKGROUND

2-Methoxy-substituted benzamides having a basic side-chain are described in the literature as drugs having an antidopaminergic action (Bernd Testa, J. Med. Chem. 26 (1983), 203–207). The best-known compound is sulpiride, but the oral availability of this is unsatisfactory.

SUMMARY OF THE INVENTION

We have found that compounds of the general formula I are distinctly superior to sulpiride in their central antidopaminergic action. This high central availability is surprising in view of the aromatic substitution pattern typical of compounds having a peripheral action (B. Pourrias, Arch. int. Pharmacodyn. 274, (1985) 223).

In the general formula I

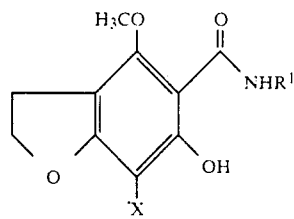

I

X is hydrogen or methoxy,
$R^1$ is a radical of the formula $$-CHR^2-CHR^3-(CR^4R^5)_n-NR^6R^7 \quad II$$

where $R^2$ to $R^5$ are each, independently of one another, hydrogen or alkyl of 1 to 6 carbon atoms, $R^6$ and $R^7$ are, independently of one another, alkyl of 1 to 6 carbon atoms, which may be branched, or benzyl which may be methyl- or halogen-substituted on the nucleus, and, in each case, one or two of $R^2$ to $R^6$ can form together with $R^7$ an alkylene chain of 2 to 6 carbon atoms which can be interrupted by an ether oxygen; n is 0 or 1.

The double bond in the furan ring can be hydrogenated.

DETAILED DESCRIPTION OF THE PREFERRED EMBODIMENTS

Thus, the following possible general structures for the group —HN—$R^1$ emerge from the general formula II:

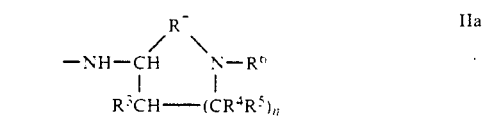

IIa

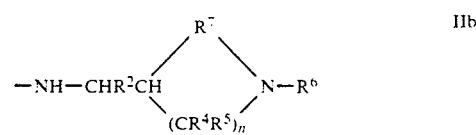

IIb

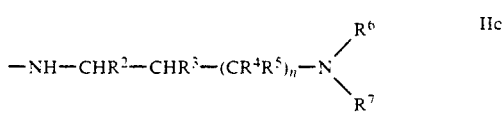

IIc

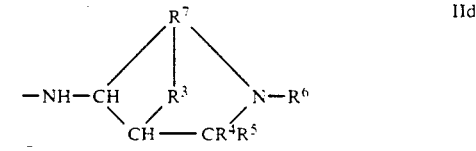

IId

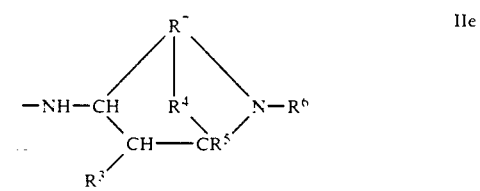

IIe

Examples are:

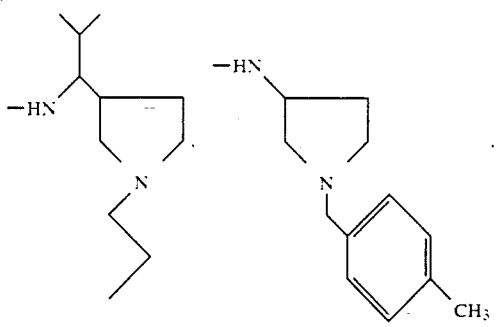

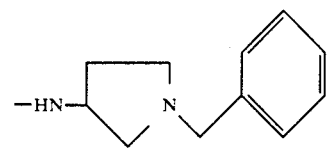

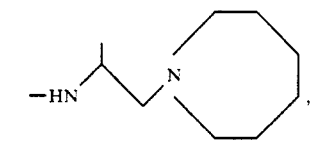

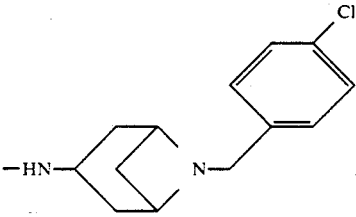

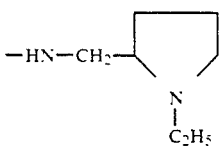

The compounds of the general formula I are prepared by reacting a reactive acid derivative III with an amine H₂N—R¹ by generally known methods.

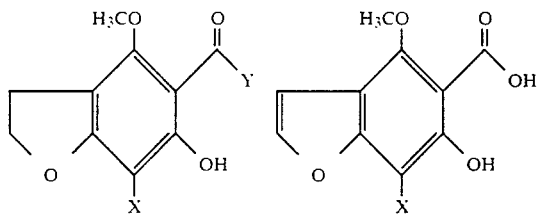

Y is a leaving group which can be displaced by nucleophiles, for example a chlorine or bromine atom, a methoxy or ethoxy group, or an oxysuccinimide, 1-imidazolyl or ethoxycarbonyloxy radical. The preparation of these acid derivatives from the acid IV, as well as the reaction thereof with amines, is known from the literature and is described, for example, in Houben-Weyl, Methoden der Org. Chemie (Methods of Organic Chemistry), 4th edition, E5, pages 941–991.

The acid IV is prepared in a simple manner by oxidative ring opening of the natural furochromones khellin Va and visnagin Vb (JACS 75, (1953) 4992).

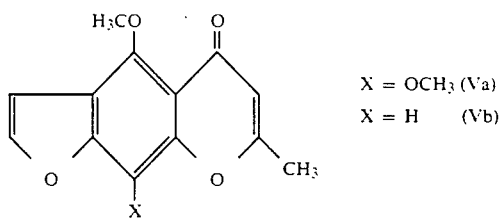

X = OCH₃ (Va)
X = H (Vb)

This means that the compounds of the general formula I can be obtained distinctly more easily than other antidopaminergic benzamides in which suitable substituents have to be introduced into the benzene ring by synthesis (J. Med. Chem. 21, (1986) 61, 25, (1982) 1280).

Compounds of the general formula I in which the furan ring is hydrogenated can be obtained in a similar manner starting from the acid

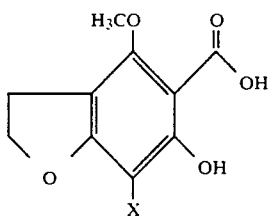

(VI)

the latter can be prepared, for example, by hydrogenation of the acid IV or of one of its salts by conventional methods.

Some of the compounds I according to the invention have a center of chirality and are obtained as racemates which can be separated into the enantiomers by conventional methods, for example by formation of diastereomeric salts with optically active acids. It is also possible to obtain the optically pure compounds I by use of the enantiomerically pure amine H₂N—R¹.

The compounds according to the invention are suitable for the therapy of a number of disorders of the central nervous system, especially for the treatment of psychotic diseases such as schizophrenia, as well as for the treatment of exogenous psychological disturbances, especially those associated with a diminution of drive. The substances can also be used for the treatment of dyskinesias (e.g. Huntington's chorea and tardive dyskinesias after neuroleptic therapy).

Further areas of use are the therapy of vomiting, of gastric ulcer or duodenal ulcer and of disturbances of motility of the gastrointestinal tract.

The therapeutic agents or compositions are prepared with the customary liquid or solid carriers of diluents and the auxiliaries customarily used in pharmaceutical technology, appropriate for the desired mode of administration and having a dosage suitable for use, in a conventional manner, for example by mixing the active compound with the solid and liquid carriers and auxiliaries customary in such products.

The agents can be administered orally, parenterally or topically. Examples of such compositions are tablets, film-coated tablets, sugar-coated tablets, capsules, pills, powders, solutions or suspensions, or solutions for infusion or injection.

The therapeutic agents can contain the compounds to be used according to the invention in a single dose of 0.03 to 3 mg per kg weight, i.e. 2 to 200 mg per tablet, and can be administered in one or more doses each day, depending on the nature and severity of the diseases.

Examples of auxiliaries customarily used in pharmaceutical technology are, for local use, alcohols such as ethanol and isopropanol, ethoxylated castor oil or ethoxylated hydrogenated caster oil, polyacrylic acid, glycerol monostearate, liquid paraffin, petrolatum, lanolin, polyethylene glycol, polyethylene glycol stearate and ethoxylated fatty alcohol, and for systemic use lactose, propylene glycol and ethanol, starch, talc and polyvinylpyrollidone. It is possible to add to the products an antioxidant, for example tocopherol and butylated hydroxyanisole or butylated hydroxytoluene, or additives to improve the flavor, stabilizers, emulsifiers, bleaching agents etc. The prerequisite is that all the substances used in the preparation of pharmaceutical compositions are toxicologically acceptable and compatible with the active compounds used.

Preparation of 2,3-dihydro-6-hydroxy-4,7-dimethoxybenzofuran -5-carboxylic acid (as precursor).

5 g of 6-hydroxy-4,7-dimethoxybenzofuran-5-carboxylic acid in 75 ml of ethanol/25 ml of H₂O/0.8 g of NaOH are hydrogenated in the presence of 1 g of Pd/C (10%) under atmospheric pressure and at 50° C. until uptake of hydrogen is complete. The mixture is filtered, the ethanol is removed by distillation, the aqueous phase is acidified, and the solid is filtered off with suction. 3.7 g of product are obtained and reacted further without purification.

N-hydroxysuccinimide ester of 6-hydroxy-4,7-dimethoxybenzofuran -5-carboxylic acid (as precursor).

A solution of 21.0 g of dicyclohexylcarbodiimide in CH₂Cl₂ is added dropwise at room temperature to 24.3 g of 6-hydroxy-4,7-dimethoxybenzofuran-5-carboxylic acid and 11.7 g of N-hydroxysuccinimide in 300 ml of CH$_2$Cl$_2$. The mixture is stirred at room temperature for 3 h, and is filtered, the filtrate is washed with water, and the solvent is removed in vacuo. Recrystallization of the residue from isopropanol provides 20.7 g of product, melting point 136° C.

The following precursors are prepared, for example, in a similar manner:

N-hydroxysuccinimide ester of 6-hydroxy-4-methoxybenzofuran -5-carboxylic acid, melting point 134° C.

N-hydroxysuccinimide ester of 2,3-dihydro-6-hydroxy -4,7-dimethoxybenzofuran-5-carboxylic acid, melting point 133° C.

EXAMPLE 1

N-[(1-Ethyl-2-pyrrolidinyl)methyl]-6-hydroxy-4,7-dimethoxybenzofuran -5-carboxamide 4.7 g of 1-ethyl-2-aminomethylpyrrolidine were added dropwise to a cooled solution of 10 g of the N-hydroxysuccinimide ester of 6-hydroxy-4,7-dimethoxybenzofuran -5-carboxylic acid in 100 ml of CH$_2$Cl$_2$. The mixture was stirred at room temperature overnight and then washed with NaHCO$_3$ solution and water. The organic phase was separated off and dried with Na$_2$SO$_4$, and the solvent was removed by distillation. The residue was recrystallized from ethanol. 7.0 g were obtained, melting point 86° C. The following compounds according to the invention were prepared in a similar manner starting from the appropriate acid and amine components.

| Example No. | —HN—R$^1$ | Melting point [°C.] |
|---|---|---|
| 2 | —HN—⟨piperidinyl-N-CH$_2$-phenyl⟩ | 212 (Hydrochloride) |
| 3 | —HN—⟨pyrrolidinyl-N-CH$_2$-phenyl⟩ | 198 (Hydrochloride) |
| 4 | —HN—⟨bicyclic-N-CH$_2$-phenyl⟩ | 138 |
| 5 | —HN—⟨bicyclic-N-CH$_2$-(4-F-phenyl)⟩ | 128 |

-continued

| Example No. | —HN—R¹ | Melting point [°C.] |
|---|---|---|
| 6 | —HN—CH(C₂H₅)—CH₂—N(azocane) | Oil |
| 7 | —HN—CH(CH₃)—CH₂—N(morpholine) | 121 |
| 8 | —HN—(tropane)—N—CH₂—C₆H₄—CH₃ (4-) | 151 |
| 9 | —HN—CH(C₂H₅)—CH₂—N(azocane) | Oil |
| 10 | —HN—(piperidin-4-yl)—N—CH₂—C₆H₄—CH₃ (4-) | 217 (Hydrochloride) |
| 11 | —HN—(piperidin-4-yl)—N—CH₂—C₆H₄—Cl (4-) | 172 (Hydrochloride) |
| 12 | —HN—(piperidin-4-yl)—N—CH₂—C₆H₄—F (4-) | 205 (Hydrochloride) |
| 13 | —HN—CH₂—(pyrrolidin-3-yl)—N—C₂H₅ | 189 (Hydrochloride) |
| 14 | —HN—(piperidin-4-yl)—N—CH₂—C₆H₅ | 204 (Hydrochloride) |

| Example No. | —HN—R[1] | Melting point [°C] |
|---|---|---|
| 15 | (pyrrolidine with N-benzyl, HN on ring) | 82 |
| 16 | (bicyclic amine with N-(4-methylbenzyl)) | 127 |
| 17 | (4-amino-1-benzylpiperidine) | 249 (Hydrochloride) |
| 18 | (3-aminomethyl-1-ethylpyrrolidine) | 153 (Hydrochloride) |
| 19 | (4-amino-1-benzylpiperidine variant) | 151 (Hydrochloride) |

We claim:

1. A benzofurancarboxamide of the formula:

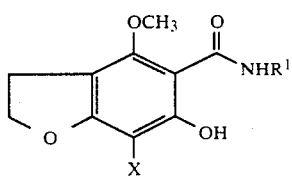

X is hydrogen or methoxy,
R[1] is a radical of the formula:

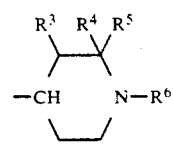

wherein $R^3$ to $R^5$ are each, independently of one another, hydrogen or $C_{1-6}$ alkyl, $R^6$ is a branched or unbranched $C_{1-6}$ alkyl, or benzyl which may be methyl- or halogen-substituted on the nucleus, and ⚌ is a single or double bond.

2. The benzofurancarboxamide of claim 1, wherein X is hydrogen.

3. The benzofurancarboxamide of claim 1, wherein X is methoxy.

4. The benzofurancarboxamide of claim 1, wherein one of $R^3$ to $R^5$ is hydrogen.

5. The benzofurancarboxamide of claim 1, wherein one of $R^3$ to $R^5$ is $C_{1-6}$ alkyl.

6. The benzofurancarboxamide of claim 1, wherein $R^6$ is a branched $C_{1-6}$ alkyl.

7. The benzofurancarboxamide of claim 1, wherein $R^6$ is an unbranched $C_{1-6}$ alkyl.

8. The benzofurancarboxamide of claim 1, wherein $R^6$ is benzyl.

9. The benzofurancarboxamide of claim 1, wherein $R^6$ is benzyl which is methyl-substituted on the nucleus.

10. The benzofurancarboxamide of claim 1, wherein $R^6$ is benzyl which the halogen-substituted on the nucleus.

11. The benzosurancarboxamide of claim 1, wherein is a single bond.

12. The benzofurancarboxamide of claim 1, wherein is a double bond.

13. A therapeutic agent, which comprises: from 2 to 200 mg of the benzofurancarboxamide of claim 1 as the active compound in combination with a pharmaceutically acceptable carrier.

* * * * *